United States Patent [19]
Pfeffer et al.

[11] Patent Number: 5,735,289
[45] Date of Patent: Apr. 7, 1998

[54] METHOD AND APPARATUS FOR ORGANIC SPECIMEN RETRIEVAL

[76] Inventors: Herbert G. Pfeffer, 14 Clubway, Hartsdale, N.Y. 10530; Peter J. Wilk, 185 W. End Ave., New York, N.Y. 10023

[21] Appl. No.: 693,486

[22] Filed: Aug. 8, 1996

[51] Int. Cl.⁶ .................................... A61B 10/00
[52] U.S. Cl. .................................... 128/751; 606/113
[58] Field of Search .................................... 128/749, 849, 128/850, 851; 606/110, 113, 114, 127, 128; 604/22, 23, 27, 171, 172

[56] References Cited

U.S. PATENT DOCUMENTS

| | | |
|---|---|---|
| 30,471 | 1/1960 | Dudley . |
| 3,472,230 | 10/1969 | Fogarty . |
| 4,611,594 | 9/1986 | Grayhack et al. . |
| 5,011,488 | 4/1991 | Ginsburg . |
| 5,037,379 | 8/1991 | Clayman et al. . |
| 5,074,867 | 12/1991 | Wilk . |
| 5,100,423 | 3/1992 | Fearnot . |
| 5,190,542 | 3/1993 | Nakao et al. . |
| 5,190,555 | 3/1993 | Wetter et al. . |
| 5,215,521 | 6/1993 | Cochran et al. . |
| 5,234,439 | 8/1993 | Wilk et al. . |
| 5,279,539 | 1/1994 | Bohan et al. . |
| 5,611,803 | 3/1997 | Heaven et al. ................ 606/110 |

*Primary Examiner*—Max Hindenburg
*Assistant Examiner*—Pamela Wingood
*Attorney, Agent, or Firm*—R. Neil Sudol; Henry D. Coleman

[57] ABSTRACT

An apparatus for specimen retrieval includes an outer impermeable pouch having an opening and a mesh enclosure having an opening. The enclosure is disposed inside the pouch and the enclosure opening is aligned with the pouch opening. The pouch includes an inflatable or resilient element for biasing the pouch opening in an open position. An element is provided for closing the pouch opening, and componentry is provided for constricting the mesh enclosure to morcellate a specimen contained therein. The constricting componentry includes componentry for retracting the enclosure or componentry for twisting the enclosure.

24 Claims, 5 Drawing Sheets

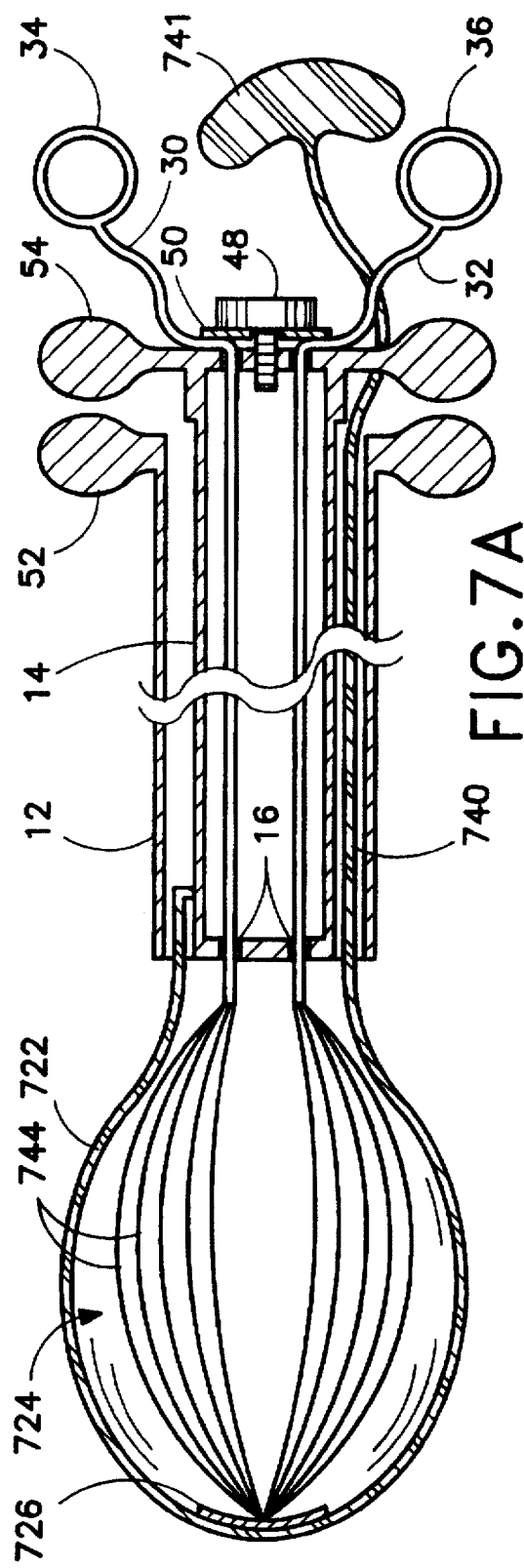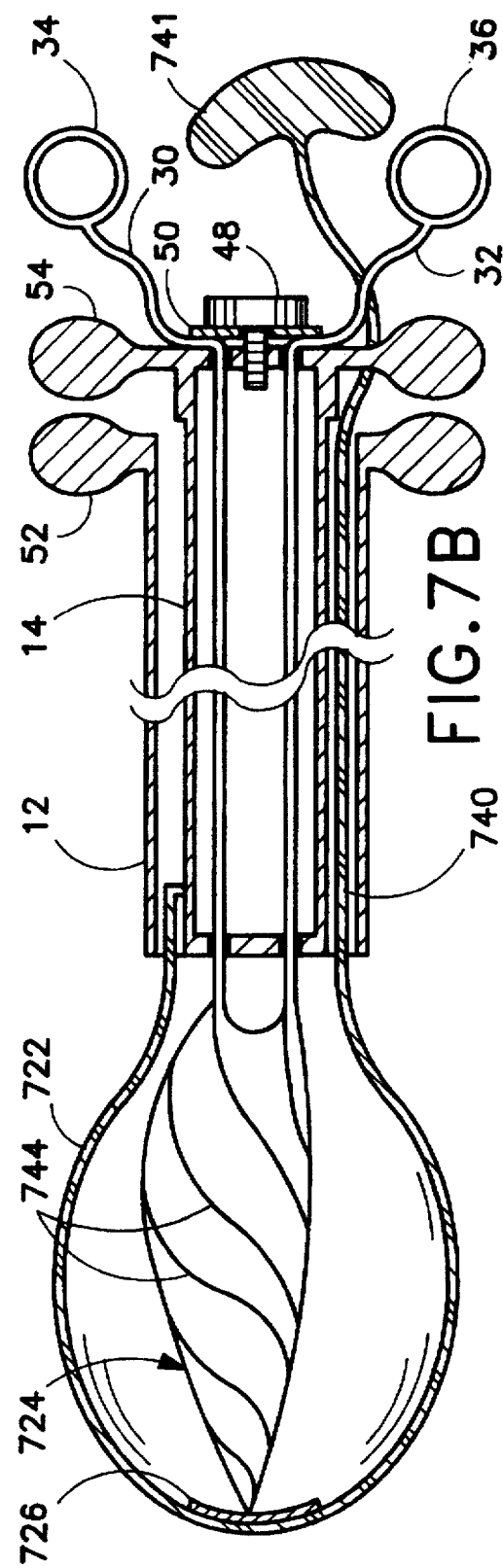

METHOD AND APPARATUS FOR ORGANIC SPECIMEN RETRIEVAL

BACKGROUND OF THE INVENTION

This invention relates to a surgical instrument or device for dissecting a relatively large organic object into smaller pieces for facilitating removal from the patient. The instrument finds particular application in laparoscopic surgery.

Laparoscopy involves the piercing of a patient's abdominal wall and the insertion of a cannula through the perforation. Generally, the cannula is a trocar sleeve which surrounds a trocar during an abdomen piercing operation. Upon the formation of the abdominal perforation, the trocar is withdrawn while the sleeve remains traversing the abdominal wall. A laparoscopic instrument, such as a laparoscope or a forceps, is inserted through the cannula so that a distal end of the instrument projects into the abdominal cavity. Generally, in a laparoscopic surgical procedure, three or four perforations are formed in the abdomen to enable deployment of a sufficient number of laparoscopic instruments to perform the particular surgery being undertaken. Each perforation is formed by a trocar which is surrounded by a sleeve, the sleeves or cannulas all remaining in the abdominal wall during the surgical procedure.

In a number of laparoscopic operations, it is desirable to remove an organic specimen from a patient. This specimen may be, for example, a tumor, a diseased organ, or a gallstone. In many cases, the specimen may be larger than the laparoscopic cannula, and it may not be possible to remove the intact specimen through the cannula. In that case, it is necessary either to form a large incision for the removal of the specimen, or to morcellate the specimen into pieces small enough to be removed through the cannula. Forming an incision large enough to remove the specimen is undesirable in that it causes additional trauma to the patient. Where a diseased specimen is to be removed, morcellation of the specimen exposes the patient to a significantly increased risk of the spread of malignancy or infection if the specimen is not adequately isolated.

OBJECTS OF THE INVENTION

An object of the present invention is to provide a surgical device for surgically removing an organic body from a patient.

Another object of the present invention is to provide such a device wherein the surgical removal can be performed laparoscopically.

Another, more particular, object of the present invention is to provide such a device which can be used in laparoscopic surgery to segment large organic bodies such as myomas. A further particular object of the present invention is to provide such a device which morcellates an organic body with a minimal risk of spreading malignancy.

These and other objects of the present invention will be apparent from the drawings and detailed descriptions herein.

SUMMARY OF THE INVENTION

An apparatus for specimen retrieval according to the present invention comprises an outer impermeable pouch with a rim defining an aperture. A mesh enclosure having an opening is disposed inside the pouch with the enclosure opening is substantially aligned with the pouch aperture. This alignment can be maintained by an attachment between the pouch and the enclosure. The pouch includes an inflatable or resilient element for biasing the pouch aperture in an open position. An element is provided for closing the pouch aperture, and componentry is provided for constricting the mesh enclosure to morcellate a specimen contained therein. The constricting componentry may include componentry for retracting the enclosure, such as a wire loop passing through a plurality of rings at the enclosure opening. Alternatively or additionally, the constricting componentry may include componentry for twisting the enclosure.

The apparatus further includes a hollow elongate shaft having a proximal end and a distal end. The pouch is positioned at the distal end, where the shaft has an opening. The closing element includes an element for pulling the pouch rim toward the opening of the shaft. The pulling element extends through the shaft.

In one conceptualization of the invention, a hollow inner shaft is provided which extends through the elongate shaft. There is a space between the inner shaft and the elongate shaft through which the pulling element extends. The retracting componentry extends through the inner shaft.

The mesh enclosure may be made of a conductive material, and an electrical power source can be attached to the mesh enclosure for cauterizing the specimen in the enclosure.

In another conceptualization of the present invention, an apparatus for specimen retrieval includes an outer impermeable pouch with a rim defining an aperture. A mesh enclosure with an opening is disposed inside the pouch. A hollow elongate shaft is provided having a proximal end and a distal end. The shaft has an opening at the distal end, and the pouch is coupled to the distal end. An element is provided for pulling the rim of the pouch toward the opening of the shaft to close the pouch opening. The pulling element extends through the shaft. Componentry is provided for constricting the mesh enclosure to morcellate a specimen contained therein. The componentry for constricting the enclosure may include componentry for twisting the enclosure.

The mesh enclosure may include a plurality of rings at the enclosure opening, in which case the constricting componentry includes a wire loop passing through the rings.

The apparatus may further include a hollow inner shaft, the inner shaft extending through the elongate shaft. There is a space between the inner shaft and the elongate shaft, through which the pulling element extends. The constricting componentry extends through the inner shaft.

In a method for use in laparoscopic specimen retrieval according the present invention, a pouch and a mesh enclosure are provided. The pouch has an aperture and the enclosure has an opening. The pouch and the enclosure are inserted into a patient. The pouch and the enclosure may be inserted through a trocar sleeve disposed through the abdominal wall of the patient. The enclosure is disposed in the pouch, and the pouch opening is aligned with the enclosure opening. An organic specimen is inserted through the pouch aperture and the enclosure opening to position the specimen in the pouch and the enclosure. The pouch aperture is closed, and the mesh enclosure is constricted to morcellate the specimen.

Where the enclosure is made of an electrically conductive material, the enclosure can be heated by passing electrical current therethrough to cauterize the specimen.

Where the pouch is releasably attached to the enclosure, the attachment of the pouch and the enclosure is released upon the closing of the pouch.

An apparatus for specimen retrieval according to the present invention, particularly for use in laparoscopic surgery, includes a first pouch having a rim defining an aperture. A second pouch has an opening communicating with the first pouch, and a mesh is mounted in the opening. A hollow elongate shaft has a proximal end and a distal end, with the pouch being coupled to the elongate shaft at the distal end of the shaft. The shaft has an opening at the distal end. Componentry is coupled to the first pouch for constricting the first pouch.

The constricting componentry can includes means for retracting the first pouch into the distal end of the elongate shaft. The means for retracting includes a strand attached to the rim of the first pouch. The strand traverses the elongate shaft.

An apparatus and method according to the present invention enable the removal of large organic specimens from a patient through a small opening, while preventing the spread of malignancy or infection in the patient.

BRIEF DESCRIPTION OF THE DRAWINGS

FIGS. 7A and 7B are schematic partial cross sectional views illustrating steps in the operation of an additional apparatus for laparoscopic specimen retrieval in accordance with the present invention.

DETAILED DESCRIPTION OF THE INVENTION

Figure 1:
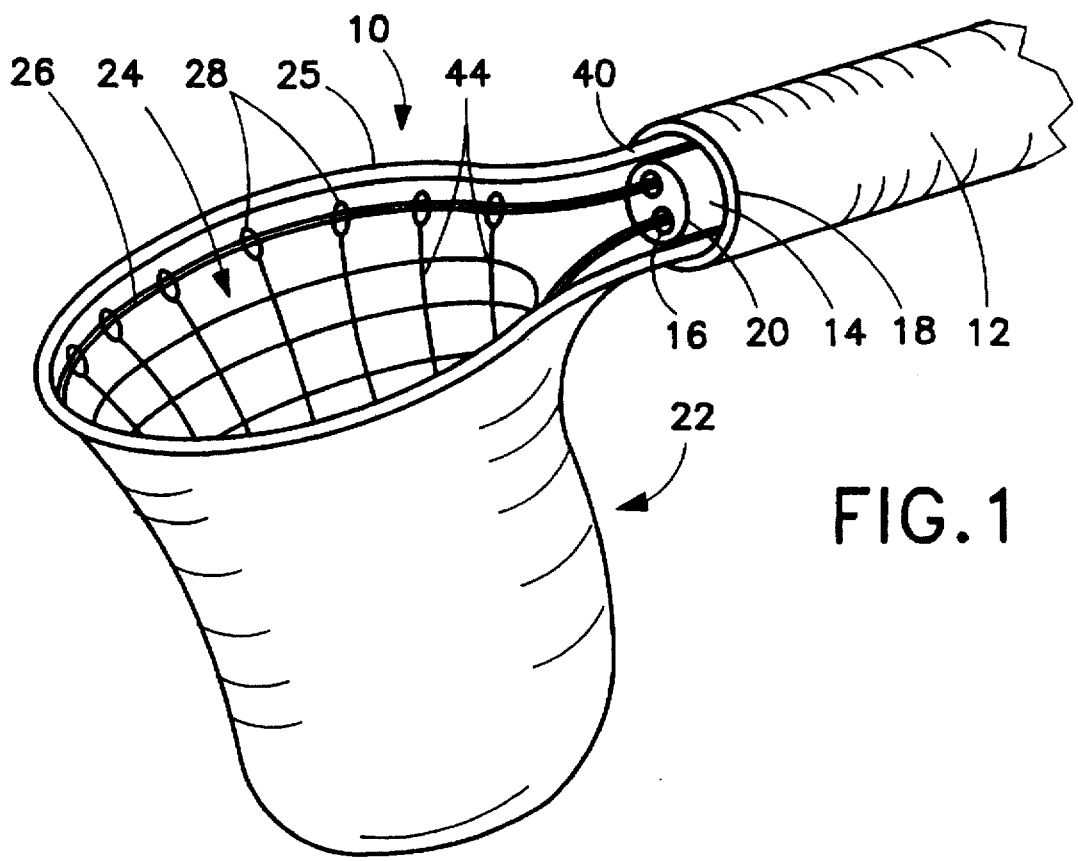
FIG. 1 is a schematic perspective view of an apparatus for laparoscopic specimen retrieval in accordance with the present invention.

As illustrated in FIG. 1, an apparatus 10 for laparoscopic specimen retrieval includes an elongate tubular outer shaft 12 with distal end 18 and a tubular inner shaft 14 with distal end 20 disposed inside outer shaft 12. A pouch 22 is provided at distal end 18 of shaft 12. Pouch 22 is provided with a rim 25 around the opening of the pouch. Rim 25 is retractable into the space between inner shaft 14 and outer shaft 12 to effectively close off pouch 22. Rim 25 acts to hold open pouch 22 and may be, for example, an inflatable annulus, in which case inflation of rim 25 holds open pouch 22, or rim 25 may be formed of a resilient material, resiliently biased into an open configuration, in which case rim 25 opens upon extension thereof from shaft 12. Pouch 22 may be provided with inflatable ribs or flexible supports in order to maintain pouch 22 in an open, deployed configuration. Rim 25 is attached to an extension 40, which extends through the space between inner shaft 14 and outer shaft 12.

A wire mesh enclosure 24 is disposed inside pouch 22. Mesh enclosure 24 has an opening substantially aligned with the opening of pouch 22 so that material passing into pouch 22 also passes into wire mesh enclosure 24. Mesh 24 includes a wire loop 26 extending around the opening of mesh 24 and attached to the rest of mesh 24 by a plurality of rings 28. The alignment of the openings of mesh 24 and pouch 22 may be ensured by an attachment between mesh 24 and pouch 22, such as through the use of an adhesive, or the use of small loops or welds (not shown). It may be desirable that any attachment between mesh 24 and pouch 22 be releasable, as further discussed below.

Wire loop 26 may for some applications be sufficient to hold open both mesh 24 and pouch 22. In that case, rim 25 can be dispensed with. Wire 26 is preferably made of a metallic substance, such as spring steel, but wire 26 can alternatively be made of any of a number of flexible materials with high tensile strength, such as, for example, nylon or aramid. The term 'wire' as used in this application is intended to encompass a flexible wire, thread, filament, or ribbon, whether of metallic or nonmetallic composition.

Figure 3:
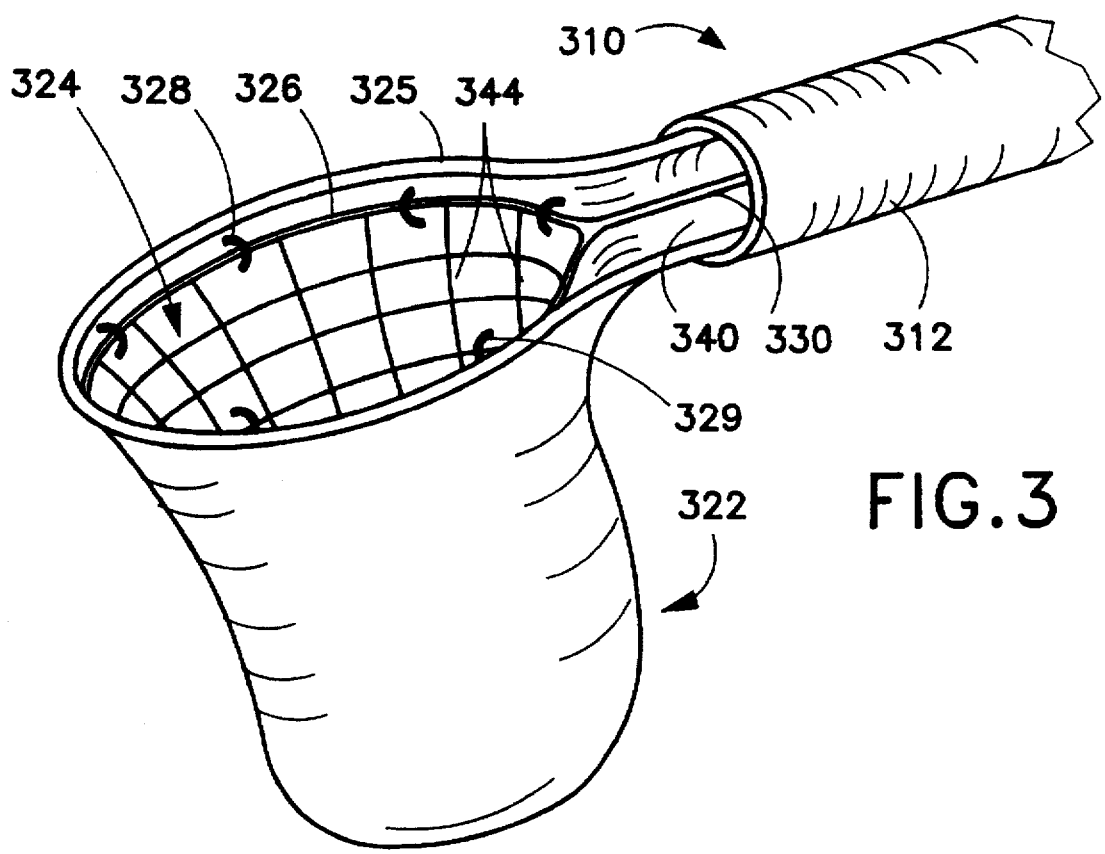
FIG. 3 is a schematic perspective view of another apparatus for laparoscopic specimen retrieval in accordance with the present invention.

Inner shaft 14 has a pair of openings 16 at distal end 20 thereof. Each of the openings 16 accepts one strand of wire loop 26. Strands 30 and 32 (FIG. 3) extend through inner shaft 14 and end in terminals 34 and 36, respectively, at a proximal end 38 of inner shaft 14.

In the use of apparatus 10 in a laparoscopic surgical operation, apparatus 10 is introduced into a patient through a cannula (not illustrated). Preferably, apparatus 10 is introduced into the patient with pouch 22 and mesh 24 retracted into outer shaft 12. Apparatus 10 can be introduced by first inserting outer shaft 12 through the cannula and subsequently introducing pouch 22, mesh 24, and inner shaft 14 into the patient through outer shaft 12. Where extension 40 is substantially rigid, pouch 22 can be deployed by pushing extension 40 manually toward distal end 18. Otherwise, pouch 22 can be deployed by forcing pouch 22 out of distal end 18 by inner shaft 14 and/or mesh 24 and wire loop 26.

Figure 2A:
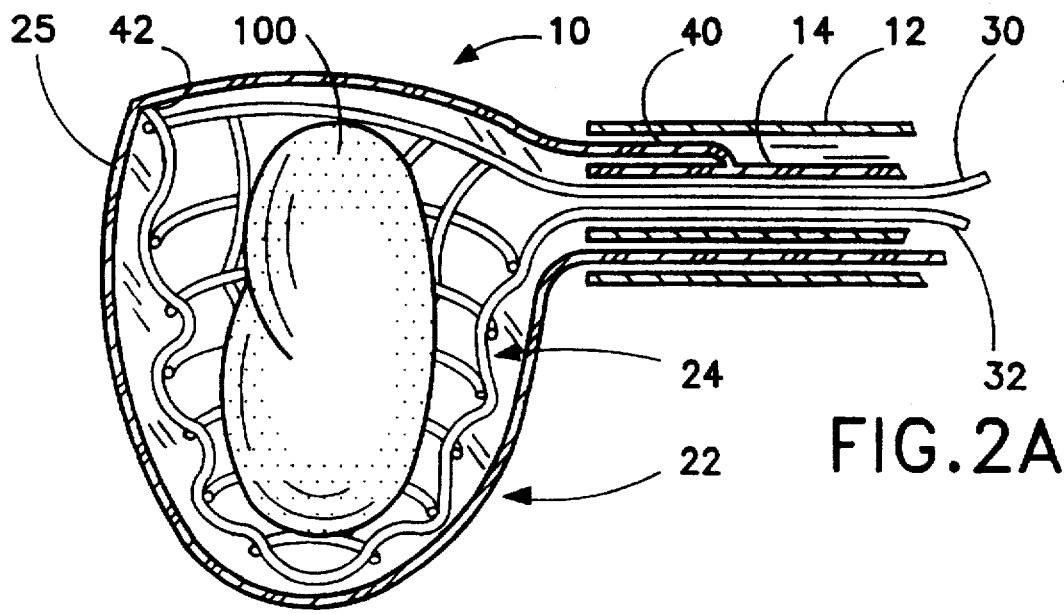
FIG. 2A–2C are schematic partial cross-sectional views illustrating laparoscopic specimen retrieval in accordance with the present invention.
Figure 2B:
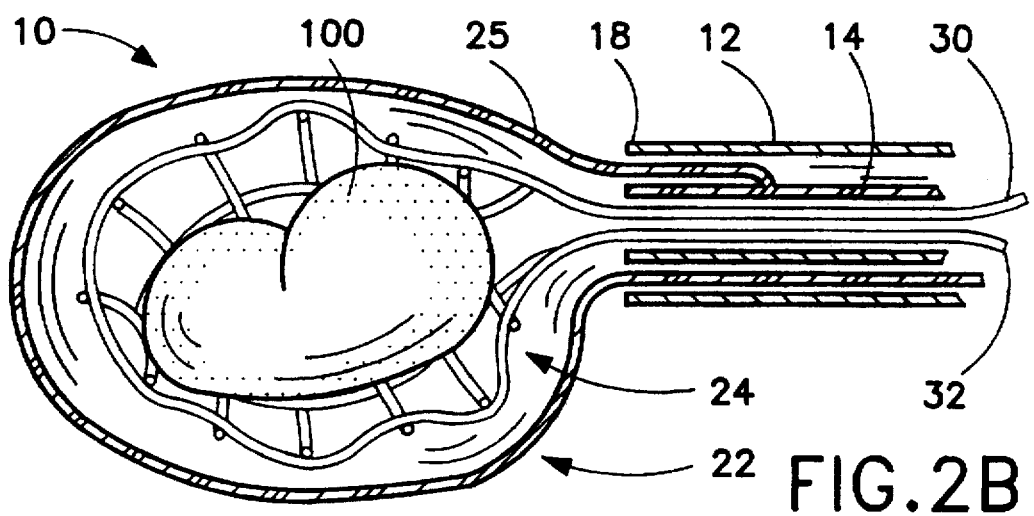
Figure 2C:
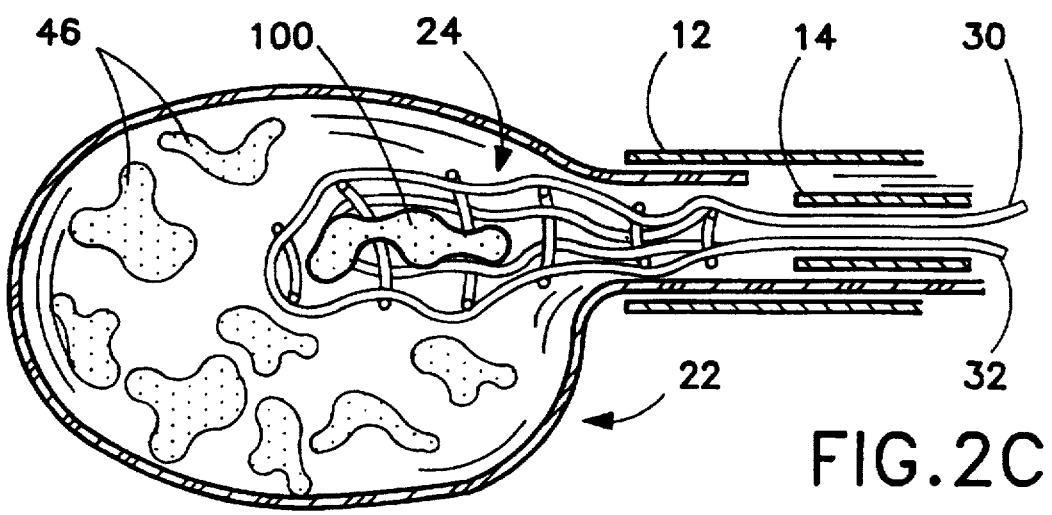

During insertion of apparatus 10 into the patient, pouch 22 and mesh 24 are typically in a collapsed configuration inside shaft 12. Following disposal of apparatus 10 into the patient, pouch 22 and mesh 24 are deployed from distal end 18 of outer shaft 12. Pouch 22 is held open by the inflation of rim 25. Mesh 24 can be held open by the resilience of wire loop 26, or by attachment of mesh 24 to pouch 22. An organic specimen 100, such as a diseased organ, a myoma, an ovarian cyst, or any other specimen which it is desirable to remove from the patient, is manipulated and positioned inside mesh 24 and pouch 22 (FIG. 2A).

Upon placement of specimen 100 in pouch 22, pouch 22 is closed by pulling extension 40 and by deflating, if necessary, rim 25. Rim 25 is pulled toward and inside distal end 18 of outer shaft 12, in particular into the space between outer shaft 12 and inner shaft 14. Accordingly, organic specimen 100 is sealed off from other bodily tissues. To ensure complete isolation of specimen 100, pouch 22 is preferably made of an impermeable and puncture resistant material, or of a combination, lamination, or layering of materials which is impermeable and puncture resistant. Where there is little or no threat of contamination, however, it may be desirable to employ a pouch made of a mesh material, with the mesh being sufficiently fine to capture morcellated pieces of the specimen. Where at least one of shafts 12 and 14 has a tapered surface (not illustrated), shafts 12 and 14 can be shifted longitudinally relative to one another to pinch the opening of pouch 22, thereby further enhancing the isolation of specimen 100.

Where mesh 24 is releasably attached to pouch 22, for example at a point 42, by an adhesive or by releasable loops (not illustrated), the pulling of rim 25 into shaft 12 causes the release of the connection at point 42, and allows pouch 22 to slip over mesh 24. Mesh 24 is closed around specimen 100 by pulling wire loop 26 via strands 30 and 32.

The closing of mesh 24 and pouch 22 may be performed simultaneously or in any order, but it is desirable that pouch 22 be entirely closed before substantial force is applied to specimen 100 by mesh 24. Once pouch 22 is entirely closed, isolating specimen 100, force is applied to wire loop 26 via strands 30 and 32 in order to retract mesh 24 toward distal end 18, thus constricting mesh enclosure 24 around specimen 100. Inner shaft 14 may be withdrawn along with mesh 24, or shaft 14 may be held stationary as mesh 24 is constricted by pulling strands 30 and 32. Since specimen 100 is too large to pass through shaft 12, as mesh 24 is retracted, threads 44 cut through specimen 100, morcellating specimen 100 into a plurality of specimen pieces 46, which are small enough to be withdrawn through a laparoscopic cannula. Pouch 22 prevents pieces 46 from contaminating bodily tissues of the patient.

Pieces 46 can be removed from the patient by, for example, aspirating the pieces through shaft 12 with or without the aid of an aspiration tube (not illustrated) inserted through shaft 12, or by first withdrawing inner shaft 14 and subsequently withdrawing pouch 22 along with its contents through shaft 12.

An apparatus 310 (FIG.3) for laparoscopic specimen retrieval includes an elongate tubular shaft 312. A pouch 322 is provided with an extension 340 extending through shaft 12. Pouch 322 is provided with a rim 325 around the opening of the pouch. Rim 325 is retractable into shaft 12 upon pulling by a surgeon of extension 340. Retraction of rim 325 into shaft 12 effectively closes off pouch 322. Rim 325 acts to hold open pouch 322 to facilitate insertion of a specimen, and may be, for example, an inflatable annulus, in which case inflation of rim 325 holds open pouch 322, or rim 325 may be formed of a resilient material, resiliently biased into an open configuration, in which case rim 325 opens upon extension thereof from shaft 312. Pouch 322 may be additionally provided with inflatable ribs or flexible supports in order to maintain pouch 322 in an open, deployed configuration.

A wire mesh enclosure 324 is disposed inside pouch 322. Mesh enclosure 324 has an opening substantially aligned with the opening of pouch 322 so that material passing into pouch 322 also passes into wire mesh enclosure 324. Mesh 324 includes a wire loop 326 extending around the opening of mesh 324 and threads 344. The alignment of the openings of mesh 324 and pouch 322 is maintained by releasable loops 328 extending from pouch 322 and encircling wire loop 326. Additional loops 329 may be provided to hold mesh 324 to pouch 322 at positions other than the openings thereof, to ensure that mesh 324 and pouch 322 are fully deployed together.

Strand 330 is attached to wire loop 326 and extends through shaft 312. In the use of apparatus 310, pouch 322 and mesh enclosure 324 are initially in a retracted position inside of shaft 312. Shaft 312 is inserted into a patient through a laparoscopic cannula (not illustrated). After disposition of shaft 312 into the patient, pouch 322 and enclosure 324 are extended from shaft 312, by pushing strand 330, for example, and are opened by virtue of the resilience of wire loop 326 and/or by inflation of rim 325. A specimen (not illustrated) is inserted into pouch 322 and enclosure 324. Pouch 322 is closed by pulling extension 340 to retract rim 325 into shaft 312. In closing pouch 322, loops 328 and 329 are broken or released, allowing pouch 322 to slip over and fully cover mesh 324.

After closing pouch 322, strand 330 is pulled to retract mesh enclosure 324 inside shaft 312. A specimen which is too large to pass into shaft 312 is cut by threads 344 into pieced which are small enough to be removed through shaft 312.

Figure 4:
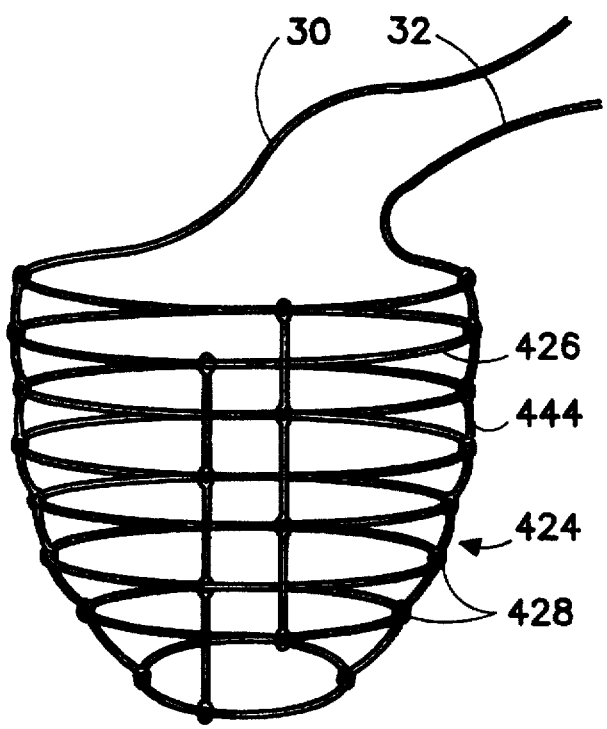
FIGS. 4, 5, and 6 are schematic perspective illustrations of mesh enclosures according to the present invention.

The morcellation of specimen 100 can be accomplished by any of a number of mesh enclosures as alternatives to mesh enclosures 24 and 324. A selected mesh enclosure may be constricted by virtue of being drawn through an opening which is smaller than the specimen to be morcellated, such as shaft 312, or the mesh may be constricted by contracting the mesh itself. FIG. 4 illustrates a mesh enclosure 424 which morcellates through contraction of the mesh itself. Mesh 424 includes a single spiral wire 426. Opposite ends of wire 426 are attached to strands 30 and 32. Of course, strands 30 and 32 may simply be a continuation of wire 426. The pulling of strands 30 and 32 tightens the spiral of wire 426 and thus constricts mesh enclosure 424. Longitudinal braces 444 may be attached to wire 426 by means of rings 428 to hold mesh 424 in shape as it constricts around a specimen and to aid in cutting through the specimen. The pulling of strands 30 and 32 may also draw mesh 424 into shaft 12, further aiding in the morcellation of the specimen.

Figure 5:
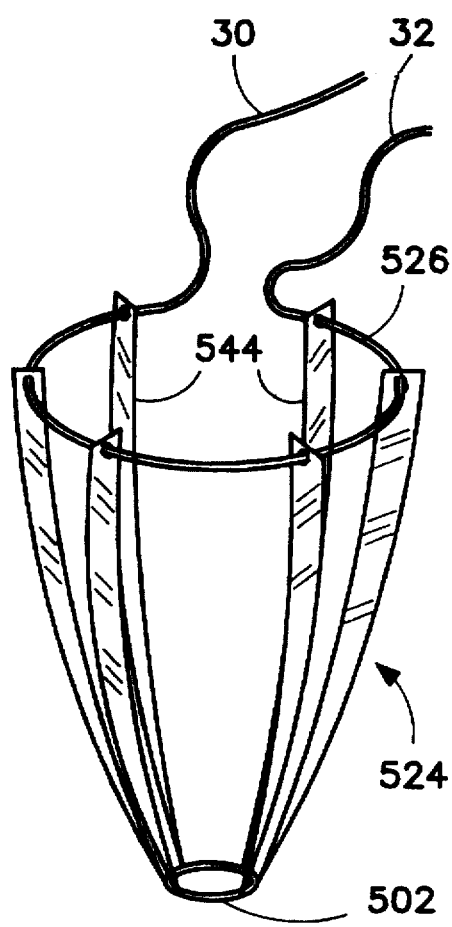
Figure 6:
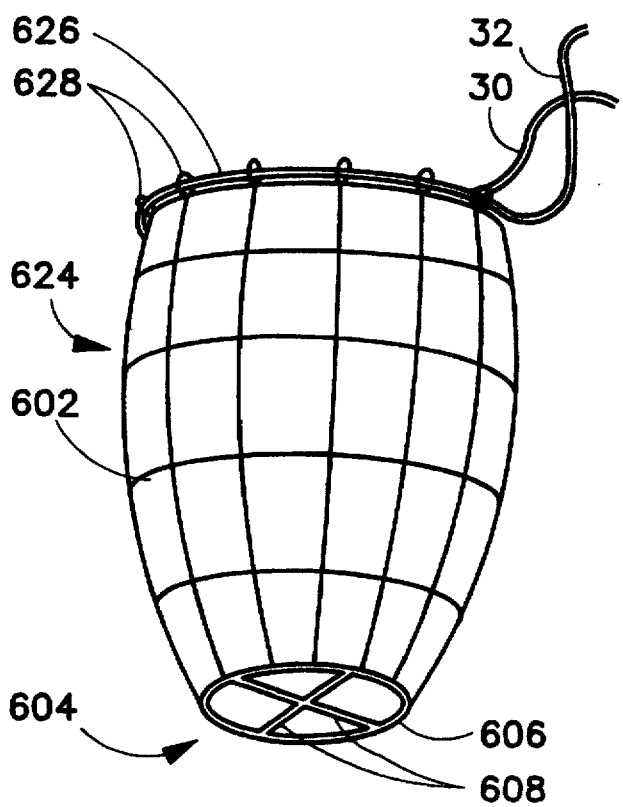

In another alternative mesh enclosure 524 (FIG. 5), a plurality of blades 544 are attached at one end to a pivot 502. Opposite pivot 502, a wire loop 526 passes through each of the blades 544. Strands 30 and 32 are attached to loop 526 and may be extensions of loop 526. Pulling on strands 30 and 32 constricts enclosure 524 and causes blades 544 to slice any specimen contained within enclosure 524. Various alternative arrangements for the mesh enclosure will be evident to practitioners of the art.

A mesh enclosure 624 may alternatively be used with apparatus 10. Mesh 624 includes a proximal web portion 602 and a distal cutting portion 604. Wire loop 626 attached to strands 30 and 32 is connected around the opening to mesh enclosure 624 by a plurality of rings 628. Web portion 602 may consist of a network of wires or filaments capable of cutting through an organic specimen, or web 602 may be a flexible, solid, woven, or perforated sheet, incapable of cutting through an organic specimen. When a specimen (not illustrated) is disposed inside enclosure 624, the enclosure is compressed by tension on strands 30 and 32 tightening wire loop 626. Under compressive tension, the specimen is forced distally toward cutting portion 604. Cutting portion 604 includes a supporting ring 606 and cutting surfaces 608. Preferably, supporting ring 606 is made of spring wire and is collapsible for insertion through shaft 12, and cutting surfaces 608 are cutting wires pulled under tension by the resilience of spring wire supporting ring 606. However, one or more of supporting ring 606 and cutting surfaces may be rigid or rigid where cutting portion 604 is small enough to be inserted through shaft 12. As the specimen is forced toward cutting portion 604, the specimen is sliced by cutting surfaces 608 and the cut portions exit mesh 624.

Various modifications of the morcellating mesh enclosures will be evident to one skilled in the art. For example, componentry can be provided which constricts the mesh enclosure by twisting the enclosure, thus cutting the specimen with a wringing action.

The morcellation of a specimen may be aided by passing electrical current through at least a portion of the mesh enclosure to cauterize the specimen. The electrical current may be provided, for example, by an electrical power source attached to one or both of strands 30 and 32. A mechanical vibrating or oscillating apparatus may be connected to strands 30 and 32 to impart a vibrating, saw-like motion to the mesh enclosure to aid in cutting through the specimen.

An instrument for laparoscopic retrieval of an organic specimen which employs a twisting action for morcellation of the specimen is illustrated in FIG. 7A–B. Grips 52 and 54 are provided on proximal ends of shafts 12 and 14, respectively. A mesh enclosure 724 with a plurality of longitudinal wires or blades 744 is attached to strands 30 and 32. Strands 30 and 32 extend into openings 16 and along inner shaft 14, to the proximal end thereof, where the strands are secured by screw 54 and washer 50. The ends of strands 30 and 32 are attached to handles 34 and 36.

A pouch 722 surrounds mesh 744. A reinforcement 726 is attached to pouch 722, and terminal ends of wires 744 are attached to reinforcement 726. Reinforcement 726 may include wires or other structural members (not illustrated) extending over the surface of pouch 722.

When a myoma or other organic specimen is inserted inside mesh 744, pouch 722 is pulled closed by an extension 740 extending through the space between shafts 12 and 14, extension 740 being attached to a handle 741 for ease of closure. The specimen may be secured tightly in mesh 744 by loosening screw 54, pulling handles 34 and 36 to tighten strands 30 and 32, and, while strands 30 and 32 are held under tension, retightening screw 54.

Once pouch 722 is closed and the specimen is in place inside mesh 744, grips 52 are held in place while grips 54 are rotated, which rotates inner shaft 14. Because the distal ends of wires 744 are prevented by reinforcement 726 from turning with shaft 14, wires 744 become twisted, causing mesh enclosure 724 to constrict. By virtue of the constriction of mesh 724, wires 744 cut into the organic specimen, morcellating the specimen into pieces which are removable through a laparoscopic cannula.

Figure 8:
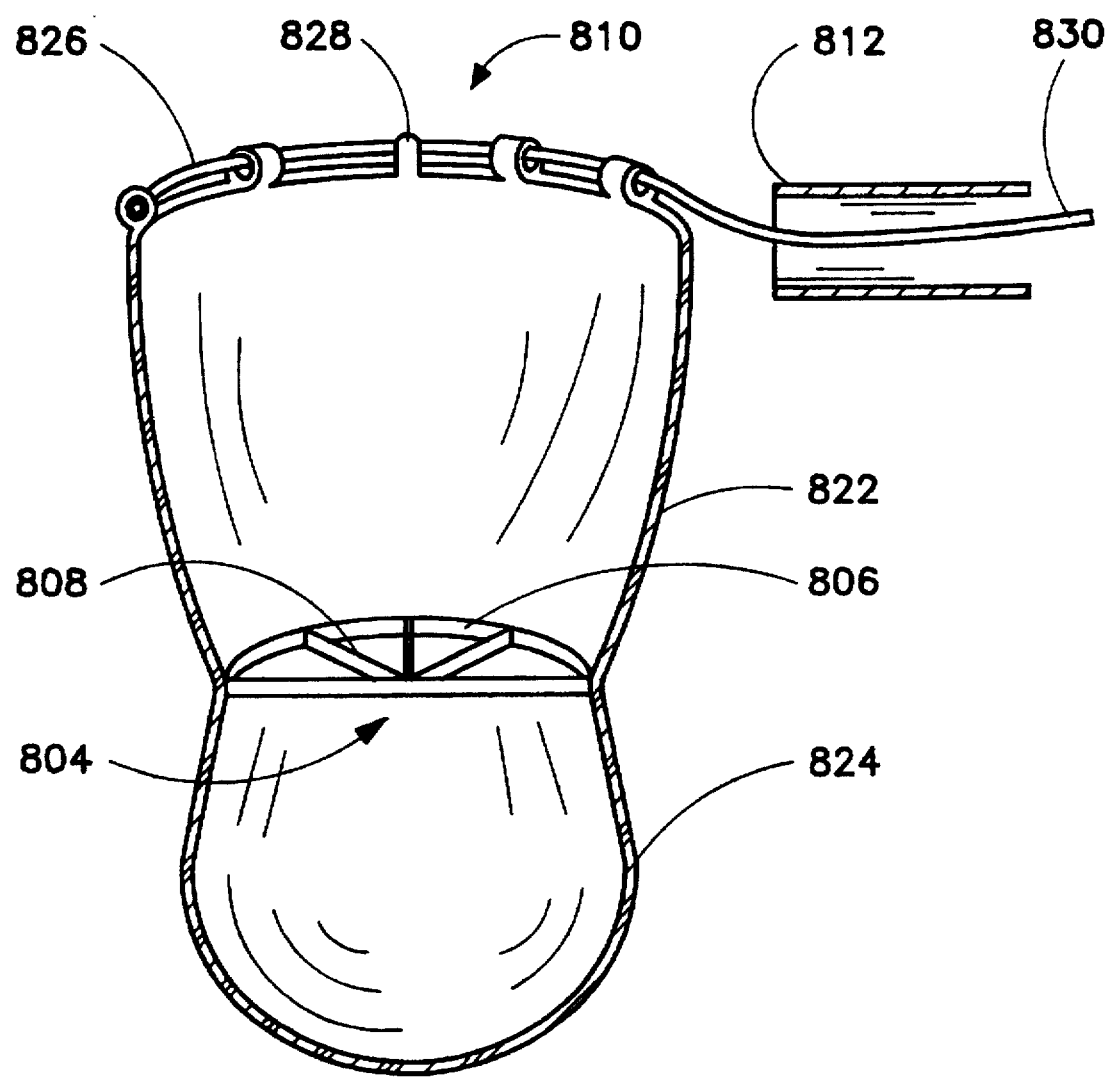
FIG. 8 is a cross-sectional view of another apparatus for laparoscopic specimen retrieval in accordance with the present invention.

As illustrated in FIG. 8, an apparatus 810 for laparoscopic specimen retrieval includes a first pouch 822 and a second pouch 824. Pouches 822 and 824 are preferably made of a flexible, impermeable material. A mesh 804 is disposed between pouch 822 and pouch 824. Pouches 822 and 824 are preferably continuous, i.e. made with a single, bag-shaped piece of material. However, it is possible to have a pouch 822 and 824, each formed of a separate piece of material and each being attached to mesh 804. First pouch 822 has an aperture surrounded by a wire loop 826 which is attached to pouch 822 via a plurality of rings 828. Loop 826 is connected to a strand 830 which extends through an elongate shaft 812. At an end of shaft 812 opposite loop 826, strand 830 is manipulable by a surgeon outside a patient. Loop 826, rings 828, and strand 830 work together as a drawstring-like closure for the aperture of pouch 822.

Mesh 804 is mounted in an opening between first pouch 822 and second pouch 824. Mesh 804 may include a plurality of blades 808 disposed radially inside a reinforcement ring 806. Alternatively, mesh 804 may take any of a number of forms, such as a wire mesh.

For the removal of an organic specimen from a patient, apparatus 810 is disposed in a patient, typically through an opening in the abdominal cavity of the patient during a laparoscopic surgical procedure. An organic specimen destined for removal from the patient is placed in pouch 822. Strand 830 is pulled from outside the patient to close pouch 822 around the specimen. Further pulling on strand 830 draws pouch 822 into elongate shaft 812. As strand 830 is drawn into shaft 812, pouch 822 is constricted by shaft 812, thus forcing the specimen through mesh 804. As the specimen passes through mesh 804, it is sliced by blades 808. Accordingly, portions of the specimen entering second pouch 824, having been morcellated by mesh 804, are of a size small enough to be withdrawn from the patient through a laparoscopic opening in the abdominal wall.

Various modifications may be made to apparatus 810, such as using a closure mechanism other than a drawstring-type closure for the aperture, or employing separate mechanisms for closing and constricting first pouch 822. The constriction of pouch 822 may be effected by techniques other than the retraction thereof into shaft 812. For example, any of the methods described above for the constriction of a mesh enclosure can be readily modified by one of ordinary skill in the art for the constriction of pouch 822, such as modifying one of the above mesh enclosures by employing thicker, non-cutting wires in place of cutting wires and dull ribs in place of blades, and surrounding pouch 822 with the modified constricting mesh enclosure. Constriction of pouch 822 can also be affected by twisting pouch 822. Resilient or inflatable means may be provided as in apparatus 22 of FIG. 1 to hold the aperture of first pouch 822 temporarily in an open position to facilitate the introduction of a specimen into the pouch.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An apparatus for specimen retrieval comprising:
   an outer pouch having a rim defining an aperture;
   a mesh enclosure in the form of a network having a maximum mesh size and an enclosure opening substantially larger than said mesh size, said mesh enclosure being disposed inside said pouch, the enclosure opening being substantially aligned with the aperture;
   means connected to said pouch for closing the aperture; and
   means connected to said enclosure for constricting said enclosure to morsellate a specimen contained therein.

2. The apparatus defined in claim 1, further comprising a hollow elongate shaft having a proximal end and a distal end, said pouch being coupled to said elongate shaft at said distal end, said elongate shaft having an opening at said distal end, said means for closing including means for pulling the rim of said pouch toward the opening of said elongate shaft, said means for pulling the rim traversing said elongate shaft.

3. The apparatus defined in claim 2 wherein said pouch includes means for biasing the aperture in an open position.

4. The apparatus defined in claim 3 wherein said means for biasing is inflatable.

5. The apparatus defined in claim 3 wherein said means for biasing is resilient.

6. The apparatus defined in claim 2 wherein said means for constricting includes means for retracting said enclosure into said elongate shaft.

7. The apparatus defined in claim 6 wherein said enclosure includes a plurality of rings at the opening of said enclosure, said means for retracting including a wire loop passing through said rings.

8. The apparatus defined in claim 6 wherein said means for constricting further includes means for twisting said mesh enclosure.

9. The apparatus defined in claim 6 further comprising a hollow inner shaft having a proximal end and a distal end, said inner shaft extending through said elongate shaft, said inner shaft and said elongate shaft having a space therebetween, said means for pulling the rim extending through the space, said means for retracting said mesh enclosure extending through said inner shaft.

10. The apparatus defined in claim 1 wherein said enclosure is made of a conductive material, further comprising an electrical power source operatively coupled to said mesh enclosure for cauterizing tissue in said enclosure.

11. The apparatus defined in claim 1 wherein said pouch is attached to said enclosure to maintain the aperture of said pouch and the opening of said enclosure in alignment.

12. The apparatus defined in claim 11 wherein said pouch is releasably attached to said enclosure, said pouch being releasable from said enclosure upon closure of the aperture of said pouch.

13. An apparatus for specimen retrieval comprising:
an outer pouch having a rim defining an aperture;
a mesh enclosure having an opening, said enclosure being disposed inside said pouch, said enclosure including a plurality of mutually parallel first tensile elements and a plurality of mutually parallel second tensile elements, said first tensile elements being disposed in crisscrossing relation with respect to said second tensile elements;
a hollow elongate shaft having a proximal end and a distal end, said pouch being coupled to said elongate shaft at the distal end of said elongate shaft, said elongate shaft having an opening at the distal end;
means connected to said pouch for pulling the rim of said pouch into the opening of said elongate shaft, said means for pulling the rim traversing said elongate shaft; and
means connected to said enclosure for constricting said enclosure to morsellate a specimen contained therein.

14. The apparatus defined in claim 13 wherein said enclosure includes a plurality of rings at the opening of said enclosure, said means for constricting including a wire loop passing through said rings.

15. The apparatus defined in claim 13 further comprising a hollow inner shaft having a proximal end and a distal end, said inner shaft extending through said elongate shaft, said inner shaft and said elongate shaft having a space therebetween, said means for pulling the pouch opening extending through the space, said means for constricting said enclosure extending through said inner shaft.

16. The apparatus defined in claim 13 wherein said means for constricting includes means for twisting said enclosure.

17. A method for use in laparoscopic specimen retrieval comprising:
providing a pouch having a rim defining an aperture and a mesh enclosure in the form of a network having a maximum mesh size and an enclosure opening substantially larger than said mesh size;
inserting said pouch and said enclosure into a patient so that said enclosure is disposed in said pouch and so that the aperture of said pouch is aligned with the opening of said enclosure;
inserting an organic specimen through the aperture of said pouch and the opening of said enclosure to position said specimen in said pouch and said enclosure;
closing the aperture of said pouch after insertion of the specimen; and
constricting said mesh enclosure to morsellate the specimen.

18. The method defined in claim 17 wherein said step of inserting includes the step of inserting said pouch and said enclosure in a collapsed configuration through a trocar sleeve disposed through the abdominal wall of the patient, further comprising opening said pouch and said enclosure in the patient.

19. The method defined in claim 17 wherein said enclosure is made of an electrically conductive material, further comprising the step of heating said enclosure by passing electrical current therethrough to cauterize the specimen.

20. The method defined in claim 17 wherein said pouch is releasably attached to said enclosure, said enclosure being opened by opening said pouch, further comprising the step of releasing the attachment of said pouch and said enclosure upon the closing of the aperture of said pouch.

21. The method defined in claim 17 wherein the step of constricting said enclosure includes the step of twisting said enclosure.

22. An apparatus for specimen retrieval comprising:
a first pouch portion having a rim defining an aperture;
a second pouch portion connected to and communicating with said first pouch portion;
a mesh element connected to said first pouch portion and said second pouch portion and partitioning said first pouch portion and said second pouch portion from one another;
a hollow elongate shaft having a proximal end and a distal end, said first pouch portion being coupled to said elongate shaft at the distal end of said elongate shaft, said elongate shaft having an opening at the distal end;
means coupled to said first pouch portion for constricting said first pouch portion to drive a specimen from said first pouch portion to said second pouch portion through said mesh element, thereby morsellating said specimen.

23. The apparatus defined in claim 22 wherein said means for constricting said first pouch includes means for retracting said first pouch into said distal end of said elongate shaft.

24. The apparatus defined in claim 23 wherein said means for retracting includes a strand attached to said rim of said first pouch, said strand traversing said elongate shaft.

* * * * *